United States Patent
Margolin et al.

(10) Patent No.: US 9,498,528 B2
(45) Date of Patent: Nov. 22, 2016

(54) TREATMENT OF MULTIPLE SCLEROSIS (MS)

(75) Inventors: David H. Margolin, Somerville, MA (US); Walter Hong, Whippany, NJ (US); Alasdair J. Coles, Cambridge (GB); Alastair Compston, Cambridge (GB); Ze'ev Shaked, San Antonio, TX (US)

(73) Assignees: GENZYME CORPORATION, Cambridge, MA (US); ALCAFLEU MANAGEMENT GMBH & CO. KG., Ot Waltersdorf (DE)

( * ) Notice: Subject to any disclaimer, the term of this patent is extended or adjusted under 35 U.S.C. 154(b) by 714 days.

(21) Appl. No.: 11/900,211

(22) Filed: Sep. 10, 2007

(65) Prior Publication Data
US 2008/0267954 A1  Oct. 30, 2008

Related U.S. Application Data

(60) Provisional application No. 60/844,251, filed on Sep. 13, 2006.

(51) Int. Cl.
A61K 39/395 (2006.01)
C07K 16/28 (2006.01)
A61K 39/00 (2006.01)

(52) U.S. Cl.
CPC ....... A61K 39/3955 (2013.01); C07K 16/2893 (2013.01); A61K 2039/505 (2013.01); A61K 2039/545 (2013.01)

(58) Field of Classification Search
None
See application file for complete search history.

(56) References Cited

U.S. PATENT DOCUMENTS

| | | |
|---|---|---|
| 5,846,534 A | 12/1998 | Waldmann et al. |
| 6,120,766 A | 9/2000 | Hale et al. |
| 2006/0057107 A1 | 3/2006 | Shaked et al. |
| 2010/0136587 A1 | 6/2010 | Margolin |
| 2013/0095507 A1 | 4/2013 | Margolin |
| 2013/0108625 A1 | 5/2013 | Margolin et al. |

FOREIGN PATENT DOCUMENTS

| | | |
|---|---|---|
| WO | WO93/10817 | 6/1993 |
| WO | WO 03/059387 A2 * | 7/2003 |
| WO | WO-2004058298 | 7/2004 |
| WO | WO-2005042581 | 5/2005 |
| WO | WO-2007143174 | 12/2007 |
| WO | WO 2008/031626 A1 | 3/2008 |
| WO | WO 2008/103292 | 8/2008 |

OTHER PUBLICATIONS

Svendsen et al (Arch Neurol. 60: 1089-1094, 2003).*
Lee et al (Brain 121: 2095-2102, 1998).*
Anderson, V.M., et al., "MRI measures of Ventricular Enlargement in Subject Presenting with Clinically Isolated Syndromes May Aid Prognosis of Multiple Scherosis Development," Multiple Sclerosis; Clinical and Laboratory Research, vol. 11(1):S54, Abstract No. P221, 21$^{st}$ Congress of the European Committee for Treatment and Research in MS and 10$^{th}$ Annual Meeting of Rehabilitation in MS, Sep. 28-Oct. 1, 2005, Thessaloniki, Greece (Sep. 2005).
Anderson, V.M., et al., "Comparison of Segmentation—and Registration-based Longitudinal Brain Atrophy Measurements in Subjects Presenting with Clinically Isolated Syndromes and Early Relapsing-remitting Multiple Sclerosis," Multiple Sclerosis; Clinical and Laboratory Research, vol. 11(1):S54-S55, Abstract No. P222, 21$^{st}$ Congress of the European Committee for Treatment and Research in MS and 10$^{th}$ Annual Meeting of Rehabilitation in MS, Sep. 28-Oct. 1, 2005, Thessaloniki, Greece (Sep. 2005).
Arnst, C., "Genzyme's Campath May Slow MS," *Business Week, Science & Technology Section*, [online] Oct. 22, 2008 [retrieved on Oct. 29, 2008]. Retrieved from http://www.businessweek.com/technology/content/oct2008/tc20081022_481728.htm.
Coles, A., et al., "Campath-1H Treatment of Multiple Sclerosis," *Neurology*, 60(5; suppl. 1), Abstract S21.005, 55$^{th}$ Annual Meeting Mar. 29-Apr. 5, 2003, Honolulu, Hawaii (Mar. 17, 2003).
Coles, A., et al., "Campath-1H Treatment of Multiple Sclerosis: Lessons from the Bedside for the Bench," *Clinical Neurol. and Neurosurg.*, 106(3):270-274 (Jun. 2004).
Coles, A., et al., "Monoclonal Antibody Treatment Exposes Three Mechanisms Underlying the Clinical Course of Multiple Sclerosis," *Ann. Neurol.*, 46(3):296-304 (Sep. 1999).
Coles, A., et al., "Pulsed Monoclonal Antibody Treatment and Autoimmune Thyroid Disease in Multiple Sclerosis," *Lancet*, 354:1691-1695 (Nov. 13, 1999).
Coles, A.J., et al., "Alemtuzumab vs. Interferon Beta-1a in Early Multiple Sclerosis," *N. Engl. J. Med.*, 359(17):1786-1801 (Oct. 23, 2008).
Coles, A.J., et al., "The Window of Therapeutic Opportunity in Multiple Sclerosis", *J. of Neurol.*, 253(1):98-108 (Jan. 2006).
Cox, A.L., et al., "Lymphocyte Homeostasis Following Therapeutic Lymphocyte Depletion in Multiple Sclerosis", *Eur. J. Immunol.*, 35(11):3332-3342 (Nov. 2005).

(Continued)

*Primary Examiner* — Daniel E Kolker
*Assistant Examiner* — Aditi Dutt
(74) *Attorney, Agent, or Firm* — Steptoe & Johnson LLP; Z. Ying Li

(57) ABSTRACT

A method for treatment of multiple sclerosis (MS) with Campath-1H with significant efficacy and a favorable safety profile is described, which offers an acceptable benefit/risk ratio. Especially described is the use of Campath-1H (alemtuzumab) for the production of a medicament for the treatment of multiple sclerosis (MS), comprising a first treatment cycle followed by at least one further treatment cycle of Campath-1H (alemtuzumab), in which each treatment cycle comprises 1-5 daily doses which are applied on consecutive days, wherein the daily dose is >0 and ≤12 mg, and wherein each treatment cycle is separated from the next cycle by at least 1-24 months. Also described are treatment regimens comprising the administration of less than 12 mg/day of Campath-1H for a period of 1-5 consecutive days.

45 Claims, 3 Drawing Sheets

(56) References Cited

OTHER PUBLICATIONS

Fox, E., et al., "Open-label, Single-arm Phase II Study of High-dose Alemtuzumab in Patients with Active Relapsing-r emitting Multiple Sclerosis Who Have Failed Licensed Beta-interferon Therapies," Multiple Sclerosis; Clinical and Laboratory Research, vol. 11(1):S172-S173, Abstract No. P650, 21$^{st}$ Congress of the European Committee for Treatment and Research in MS and 10$^{th}$ Annual Meeting of Rehabilitation in MS, Sep. 28-Oct. 1, 2005, Thessaloniki, Greece (Sep. 2005).

Fox, R., et al. "Diffusion Tensor Measurements in Post-mortem Brain," Multiple Sclerosis; Clinical and Laboratory Research, vol. 11(1):S139-S140, Abstract No. P537, 21$^{st}$ Congress of the European Committee for Treatment and Research in MS and 10$^{th}$ Annual Meeting of Rehabilitation in MS, Sep. 28-Oct. 1, 2005, Thessaloniki, Greece (Sep. 2005).

Genzyme and Bayer Schering Pharmaceuticals, "A Phase II Study Comparing Low- and High-Dose Alemtuzumab and High-Dose Rebit® in Patients with Early, Active Relapsing-Remitting Multiple Sclerosos," ClinicalTrials.gov, Indentifier NCT00050778 [online] [retrieved on Oct. 31, 2008]. Retrieved from http://www.clinical_trials.gov/ct2/show/NCT00050778.

Hale G., and Waldmann, H., From Laboratory to Clinic: The Story of Campath-1H in *Methods in Molecular Medicine; Diagnostic and Therapeutic Antibodies*, George, A.J.T., et al., eds. (NJ:Humana Press, Inc.), vol. 40:243-266 (2000).

Hale G., et al., "The Campath-1 Antigen (CD52)", *Tissue Antigens*, 35:118-127 (Mar. 1990).

Moreau, T., et al., "Preliminary Evidence from Magnetic Resonance Imaging for Reduction in Disease Activity After Lymphocyte Depletion in Multiple Sclerosis," *Lancet*, 344:298-301 (Jul. 30, 1994).

Moreau, T., et al., "Transient Increase in Symptoms Associated with Cytokine Release in Patients with Multiple Sclerosis," *Brain*, 119:225-237 (Feb. 1996).

National Multiple Sclerosis Society, "General Information—Just the Facts: 2007-2008." Published by National MS Society (Sep. 2008).

O'Donnell, L.E., et al., "Safety and Management of Campath-1H Infusion Reactions in MS Patients," Platforms, The Art and Science of Multiple Sclerosis Meeting, Toronto, Canada, Presentation P12, Jun. 2-6, 2004.

Press Release, "Genzyme Reports Interim Results from Trial of Campath(R) for Multiple Sclerosis," Medical News Today [online] Sep. 15, 2006 [retrieved on Oct. 28, 2008]. Retrieved from http://www.medicalnewstoday.com/articles/51887.php.

The Multiple Sclerosis Resource Center, "Campath," pp. 1-11, [online] Dec. 4, 2007 [retrieved on Apr. 12, 2007]. Retrieved from http://www.msrc.do.uk/index.cfm?fuseaction=show&pageid=1307.

Jan. 10, 2008, Notification of Transmittal of the International Search Report and the Written Opinion of the International Searching Authority, or the Declaration, PCT/EP2007/008084.

Aug. 6, 2008 (completion date), International Preliminary Report on Patentability, PCT/EP2007/008084.

Ilex Pharmaceuticals, L.P. (San Antonio, TX 78229), Campath Draft Package Insert (PK/Safety), pp. 1-14 (Apr. 2004).

Compston, A., et al., "Two Year Interim Analysis of Thyroid Abnormalities in a Trial of Alemtuzumab vs High-Dose Interferon-Beta-1a, for Treatment of Relapsing-Remitting Multiple Sclerosis," *The 22nd Congress of the European Committee for Treatment and Research in Multiple Sclerosis (ECTRIMS)*, Madrid, Spain, Abstract No. P799 (Sep. 27-30, 2006).

Fox, E., et al., "ITP Following Treatment of Multiple Sclerosis Patients with Alemtuzumab in CAMMS22: Case Reports and Risk Management Plan Implementation," *The 22nd Congress of the European Committee for Treatment and Research in Multiple Sclerosis (ECTRIMS)*, Madrid. Spain, Abstract No. P800 (Sep. 27-30, 2006).

Coles, A., and the CAMMS223 Study Group, "Efficacy of Alemtuzumab in Treatment-Naive Relapsing-Remitting Multiple Sclerosis: Analysis After Two Years of Study CAMMS223," *The 59th Annual Meeting of the American Academy of Neurology (AAN)*, Boston, MA, Abstract No. S12.004 (Apr. 28-May 5, 2007).

Coles, A., and the CAMMS223 Study Group, "Two-Year Interim Analysis of Thyroid Abnormalities in a Trial of Alemtuzumab vs. High-Dose Interferon Beta-1a for Treatment of Relapsing-Remitting Multiple Sclerosis," *The 59th Annual Meeting of the American Academy of Neurology (AAN)*, Boston, MA, Abstract No. P06.087 (Apr. 28-May 5, 2007).

Compston, A. and the CAMMS223 Study Group, "Autoantibody Prediction of Risk for Thyroid Adverse Events After Alemtuzumab Treatment for Relapsing Multiple Sclerosis," *The 59th Annual Meeting of the American Academy of Neurology (AAN)*, Boston, MA, Abstract No. P06.091 (Apr. 28-May 5, 2007).

Sullivan, H., and the CAMMS223 Study Group, "ITP Following Treatment of Multiple Sclerosis Patients with Alemtuzumab in CAMMS223: Case Reports and Risk Management Plan Implementation," *The 59th Annual Meeting of the American Academy of Neurology (AAN)*, Boston, MA, Abstract No. 532.004 (Apr. 28-May 5, 2007).

Bass, A., D.-D., for the CAMMS223 International Study Group, "Consistend Efficacy of Alemtuzumab in Relapsing-Remitting Multiple Sclerosis Across Major Demographic Subgroups," *The 12$^{th}$ Annual Meeting of the Americas Committee for the Treatment and Research in Multiple Sclerosis (ACTRIMS)*, Washington, D.C. (Jun. 2, 2007).

Coles, A.J., for the CAMMS223 Study Group, et al., "Alemtuzumab Improved Multiple Sclerosis Functional Composite Scores and Delayed Time to First Relapse at 2-Year Interim Analysis Compared to Subcutaneous Interferon Beta-1a," *The 23rd Congress of the European Committee for the Treatment and Research in Multiple Sclerosis (ECTRIMS)*, Prague, Czech Republic, Abstract No. P557 (Oct. 11-14, 2007).

Coles, A., for the CAMMS223 International Study Group, "Efficacy of Alemtuzumab in Relapsing-Remitting Multiple Sclerosis is Independent of Baseline Status," *The 17$^{th}$ Meeting of the European Neurological Society (ENS)*, Rhodes, Greece, Abstract No. Abs945 (Jun. 16-20, 2007).

Coles, A., and the CAMMS223 Study Group, "Alemtuzumab Compared with Subcutaneous High-Dose IFNB-1a in Treatment-Naive Relapsing-Remitting Multiple Sclerosis: Primary Efficacy Outcomes of CAMMS223 at 3 Years", *The 60$^{th}$ Annual Meeting of the American Academy of Neurology (AAN)*, Chicago, IL, Abstract No. S22.006 (Apr. 12-19, 2008).

Fox, E.J., for the CARE-MS$^{SM}$ Steering Committee and CARE-MS$^{SM}$ Design Team, "The CARE-MS$^{SM}$ II Trial (Comparison of Alemtuzumab and Rebif® Efficacy in Multiple Sclerosis): Design of a Phase 3, Open-Label, Rater and Dose-Blinded Study of Alemtuzumab in Patients with MS Who Have Relapsed on Therapy," *The 60$^{th}$ Annual Meeting of the American Academy of Neurology (AAN)*, Chicago, IL, Abstract No. P02.150 (Apr. 12-19, 2008).

Havrdova, E., for the CARE-MS$^{SM}$ Steering Committee and Care-MS$^{SM}$ Design Team, "The CARE-MS$^{SM}$ I Trial (Comparison of Alemtuzumab and Rebif® Efficacy in Multiple Sclerosis): Design of a Phase 3, Open-Label, Rater-Blinded Study of Alemtuzumab Patients in Treatment- Naïve Patients with Relapsing MS," *The 60$^{th}$ Annual Meeting of the American Academy of Neurology (AAN)*, Chicago, IL, Abstract No. P02.171 (Apr. 12-19, 2008).

Cooper, J., for the CAMMS223 International Study Group, "Efficacy with Early Use of Alemtuzumab in MS is Independent of Baseline Disease Status," *The 22$^{nd}$ Annual Meeting of the Consortium of Multiple Sclerosis Centers (CMSC)*, Denver, CO, Abstract No. P11 (May 28-May 31, 2008).

Brinar, V., on behalf of the CAMMS223 Study Group, Alemtuzumab Phase 2 Extension Study Design (CAMMS223): Assessing Long-Term Outcomes and Potential Benefits of Additional Alemtuzumab Treatment in Patients with Relapsing-Remitting Multiple Sclerosis, *The World Congress on the Treatment and Research in Multiple Sclerosis (WCTRIMS)*, Montreal, Canada, Abstract No. P17 (Sep. 17-20, 2008).

(56) References Cited

OTHER PUBLICATIONS

Selmaj, K, on behalf of the CAMMS223 Study Group, "Alemtuzumab Significantly Increases the Proportion of Clinically Disease-Free Patients with Relapsing-Remitting MS Compared to Subcutaneous Interferon Beta-1a: Results from a Phase 2 Study," *The World Congress on the Treatment and Research in Multiple Sclerosis (WCTRIMS)*, Montreal, Canada, Abstract No. P55 (Sep. 17-20, 2008).

Vladic, A., on behalf of the CAMMS223 Study Group, "Early Treatment of Multiple Sclerosis with Alemtuzumab Significantly Improves Patient Functioning and Self-Reported Quality of Life Compared to SC Interferon Beta-1a," *The World Congress on the Treatment and Research in Multiple Sclerosis (WCTRIMS)*, Montreal, Canada, Abstract No. P528 (Sep. 17-20, 2008).

Coles, A., for the CAMMS223 International Study Group, "Consistent Efficacy with Early Use of Alemtuzumab in Relapsing-Remitting Multiple Sclerosis Across Major Demographic Subgroups," *The 18th Meeting of the European Neurological Society (ENS)*, Nice, France, Abstract No. Abs894 (Jun. 7-11, 2008).

Coles, A., on behalf of the CAMM223 Study Group, "Alemtuzumab Induces a Sustained Reduction in Disability in Patients with Relapsing Remitting Multiple Sclerosis," *The 61st Annual Meeting of the American Academy of Neurology (AAN)*, Seattle, WA, Abstract No. P06.145 (Apr. 25-May 2, 2009).

Wray, S., on behalf of the CAMMS223 Study Group, "Two Annual Cycles of Alemtuzumab Yield Durable Treatment Response 24 Months After Last Dose," *The 61st Annual Meeting of the American Academy of Neurology (AAN)*, Seattle, WA, Abstract No. P07.143 (Apr. 25-May 2, 2009).

Bass, A., on behalf of the CAMMS223 Study Group, "Effect of Alemtuzumab on Quality of Life in Patients with Relapsing Remitting Multiple Sclerosis," *The 14th Annual Meeting of the Americas Committee for the Treatment and Research in Multiple Sclerosis (ACTRIMS)*, Atlanta, GA, (May 27-May 30, 2009).

Fox. E, on behalf of the CAMMS223 Study Group, "Alemtuzumab improves EDSS Functional System Scores Better Than Interferon Beta-1a in Patients with RRMS," *The 14th Annual Meeting of the Americas Committee for the Treatment and Research in Multiple Sclerosis (ACTRIMS)*, Atlanta, GA. (May 27-May 30, 2009).

Coles, A., on behalf of the CAMMS223 Study Group, "Alemtuzumab Reverses Pre-Existing Disability in Relapsing-Remitting Multiple Sclerosis Patients Independent of Relapse History," *The 25th Congress of the European Committee for the Treatment and Research in Multiple Sclerosis (ECTRIMS)*, Dusseldorf, Germany, Abstract No. P465 (Sep. 9-12, 2009).

Coles, A., on behalf of the CAMMS223 Study Group, "Alemtuzumab Treatment Benefit is Durable: Primary Efficacy Outcomes of CAMMS223 at 4 Years," *The 25th Congress of European Committee for the Treatment and Research in Multiple Sclerosis (ECTRIMS—Late Breaking Abstract)*, Dusseldorf, Germany, Abstract No. P890 (Sep. 9-12, 2009).

Selmaj, K,. on behalf of the CAMMS223 Study Group, "Immunogenicity of Alemtuzumab Treatment for Relapsing Remitting Multiple Sclerosis: No Effect on Efficacy or Safety," *The 25th Congress of the European Committee for the Treatment and Research in Multiple Sclerosis (ECTRIMS)*, Dusseldorf, Germany, Abstract No. P811 (Sep. 9-12, 2009).

Wray, S., on behalf of the CAMMS223 Study Group, "A Descriptive Analysis of Infectious Adverse Events in Alemtuzumab-treated Multiple Sclerosis Patients," *The 25th Congress of the European Committee for the Treatment and Research in Multiple Sclerosis (ECTRIMS)*, Dusseldorf, Germany, Abstract No. P812 (Sep. 9-12, 2009).

Wynn, D., on behalf of the CAMMS223 Study Group, "Alemtuzumab Increases the Likelihood of Sustained Reduction in Disability, Independent of Baseline Demographic or Disease Characteristcs," *The 25th Congress of the European Committee for the Treatment and Research in Multiple Sclerosis (ECTRIMS)*, Dusseldorf, Germany, Abstract No. P466 (Sep. 9-12. 2009).

Hutton, G., "The CARE-MS$^{SM}$ II Trial (Comparison of Alemtuzumab and Rebif® Efficacy in Multiple Sclerosis): Design of a Phase 3, Open-Label, Rater-Blinded Study of Alemtuzumab in Patients with MS Who Have Relapsed on Therapy," *The 19th Meeting of the European Neurological Society (ENS)*, Milan, Italy, Abstract No. Abs771 (Jun. 20-24, 2008).

LaGanke, C., on behalf of the CAMMS223 Study Group, "Exploring Alemtuzumab's Long Term Efficacy and Safety: Design of the CARE-MS Extension Study," *The 62nd Annual Meeting of the American Academy of Neurology (AAN)*, Toronto, Canada, Abstract No. P06.164, (Apr. 10-17, 2010).

Fox, E., on behalf of the CAMMS223 Study Group, "Long-term Follow-up of Immune Thrombocytopenia after Treatment of Multiple Sclerosis Patients with Alemtuzumab in CAMMS223," *The 62nd Annual Meeting of the American Academy of Neurology (ANN)*, Toronto, Canada, Abstract No. P05.036, (Apr. 10-17, 2010).

Fox, E., on behalf of the CAMMS221 Study Group, "Sustained Positive Effects of Alemtuzumab on Diverse Neurological Functions in Relapsing-Remitting Multiple Sclerosis Patients," *The 62nd Annual Meeting of the American Academy of Neurology (ANN)*, Toronto, Canada, Abstract No. P05.036, (Apr. 10-17, 2010).

Brinar, V., on behalf of the CAMMS223 Study Group, "Benefits of Alemtuzumab are Evident Even in Relapsing-Remitting Multiple Sclerosis Patients Who Experience Autoimmune Adverse Events," *The 62nd Annual Meeting of American Academy of Neurology (AAN)*, Toronto, Canada, Abstract No. P03.114, (Apr. 10-17, 2010).

Khan, O, on behalf of the CAMMS223 Study Group, "Alemtuzumab Reduces Disease Progression in RRMS; Long-Term Results of the CAMMS233 Trial," *The 62nd Annual Meeting of the Amerieen Academy of Neurology (AAN)*, Toronto, Canada, Abstract No. P04.213, (Apr. 10-17, 2010).

Twyman, C.I., on behalf of the CAMMS223 Study Group, "Durable Efficacy of Alemtuzumab Treatment: Clinical Efficacy at Four Years," *The 24th Annual Meeting of the Consortium of Multiple Sclerosis Centers (CMSC)*, San Antonio, TX, Abstract No. S136, (Jun. 2-5, 2010).

Fox, E., on behalf of the CAMMS223 Study Group, "Alemtuzumab and Immune Thrombocytopenia Safety Monitoring Program in CAMMS223," *The 24th Annual Meeting of the Consortium of Multiple Sclerosis Centers (CMSC)*, San Antonio, TX, Abstract No. S42, (Jun. 2-5, 2010).

LaGanke, C., on behalf of the CAMMS223 Study Group, "CARE-MS Extension Study: As-Needed RRMS Treatment Paradigm with Alemtuzumab," *The 24th Annual Meeting of the Consortium of Multiple Sclerosis Centers (CMSC)*, San Antonio, TX, Abstract No. W13, (Jun. 2-5, 2010).

Mayer L,. "Alemtuzumab Infusion in MS: Nursing Perspective on Infusion-Associated Reactions," *The 24th Annual Meeting of the Consortium of Multiple Sclerosis Centers (CMSC)*, San Antonio, TX, Abstract No. S88, (Jun. 2-5, 2010).

Vladic, A, on behalf of the CAMMS223 Study Group. "Significant Treatment Effects of Alemtuzumab Amongst RRMS Patients Who Experience Thyroid Abnormalities," *The 20th Meeting of the European Neurological Society (ENS)*, Berlin, Germany, Abstract No. Abs745 (Jun. 19-23, 2010).

Havrdove, E., et al., "Alemtuzumab for Relapsing-Remitting Multiple Sclerosis: CARE-MS I Baseline Demographics and Disease Characteristics," *The 26th Congress of the European Committee for the Treatment and Research in Multiple Sclerosis (ECTRIMS)*, Gothenburg, Sweden, Abstract No. Abs Nr 1250, (Oct. 13-16, 2010).

Coles, A., on behalf of the CAMMS223 Study Group, "Alemtuzumab Long-term Safety and Efficacy: Five Years of CAMMS223 Trial," *The 26th Congress of the European Committee for the Treatment and Research in Multiple Sclerosis (ECTRIMS)*, Gothenburg, Sweden, Abstract No. Abs Nr 1245, (Oct. 13-16, 2010).

Meyer, D. and Coles. A. on behalf of the CAMMS223 Study Group, "Case Report of Anti-Glomerular Basement Membrane Disease Following Alemtuzumab Treatment," *The 26th Congress of the European Committee for the Treatment and Research in Multiple Sclerosis (ECTRIMS)*, Gothenburg, Sweden, Abstract No. Abs Nr 1251. (Oct. 13-16, 2010).

(56) References Cited

OTHER PUBLICATIONS

Wingerchuk, D.M., on behalf of the CAMMS223 Study Group, "Efficacy of Alemtuzumab in Highly Active Relapsing-Remitting Multiple Sclerosis Patients in CAMMS223," *The 26th Congress of the European Committee for the Treatment and Research in Multiple Sclerosis (ECTRIMS)*, Gothenburg, Sweden, Abstract No. Abs Nr 1252, (Oct. 13-16, 2010).

Herbert, J. and Wynn, D., on behalf of the CAMMS223 Study Group, "Alemtuzumab's Efficacy in CAMMS223 as Assessed with the Multiple Sclerosis Severity Score," *The 26th Congress of the European Committee for the Treatment and Research in Multiple Sclerosis (ECTRIMS)*, Gothenburg, Sweden, Abstract No. Abs Nr 1254, (Oct. 13-16, 2010).

Wynn, D., on behalf of the CAMMS223 Study Group, "Disability Progression-Free Efficacy of Alemtuzumab in Relapsing-Remitting Multiple Sclerosis Patients in CAMMS223," *The 26th Congress of the European Committee for the Treatment and Research in Multiple Sclerosis (ECTRIMS)*, Gothenburg, Sweden, Abstract No. Abs Nr 1263, (Oct. 13-16, 2010).

Rao, S. et al., "Differential Sensitivity of Human PBMC Subsets to Alemtuzumab-Mediated Cytotoxicity," *The 26th congress of the European Committee for the Treatment and Research in Multiple Sclerosis (ECTRIMS)*, Gothenburg, Sweden, Abstract No, Abs Nr 1239, (Oct. 13-16, 2010).

Turner, M.J, et al., "Analysis of Immune Competence Following Alemtuzumab Treatment in huCD52 Transgenic Mice," *The 26th Congress of the European Committee for the Treatment and Research in Multiple Sclerosis (ECTRIMS)*, Gothenburg, Sweden, Abstract No. Abs Nr 1240, (Oct. 13-16, 2010).

Havari, E., et al., "Impact of Alemtuzumab Treatment on the Survival and Function of Human Tregs in vitro," *The 26th Congress of the European Committee for the Treatment and Research in Multiple Sclerosis (ECTRIMS)*, Gothenburg, Sweden, Abstract No. Abs Nr 1238, (Oct. 13-16, 2010).

Lake, S.L., et al., "Analysis of EDSS Measurements from CAMMS223: Application of a Markov Transition Model for Repeated Ordinal Data," *The 26th Congress of the European Committee for the Treatment and Research in Multiple Sclerosis (ECTRIMS)*, Gothenburg, Sweden, Abstract No. Abs Nr 1243, (Oct. 13-16, 2010).

Coles, "Leukocyte Dynamics Following Alemtuzumab Treatment of Relapsing-Remitting Multiple, Sclerosis in a Phase 2 Study (CAMMS223)," *The 62nd Annual Meeting of the American Academy of Neurology (AAN)*, Toronto, Canada, Abstract No. P06.172, (Apr. 10-17, 2010).

Turner, "Detailed analysis of CD52 expression and cellular depletion/repopulation after alemtuzumab treatment in huCD52 transgenic mice," *The 62nd Annual Meeting of the American Academy of Neurology (AAN)*, Toronto, Canada, Abstract No. P06.207 (Apr. 10-17, 2010).

Genzyme Corporation Press Release. "Genzyme Completes Acquisition of ILEX Oncology, Inc.", Issued Dec. 21, 2004, Cambridge, MA.

Genzyme Corporation and Schering AG Press Release, "Genzyme and Schering AG Announce Interim Results from Trial of Campath for Multiple Sclerosis: Data Suggest Strong Treatment Effect for Patients Using Campath; Serious Adverse Events in Trial Require Comprehensive Risk Management Plan", Issued Sep. 16, 2005, Cambridge, MA and Berlin, Germany.

Genzyme Corporation Press Release. "Genzyme Reports Interim Results from Trial of Campath® for Multiple Sclerosis: Two-Year, Pre-Planned Interim Analysis Demonstrates Robust, Statistically Significant Treatment Effect of Campath Compared to Rebif®", Issued Sep. 14, 2006, Cambridge, MA.

Genzyme Corporation and Bayer HealthCare Pharmaceutical Press Release. "Genzyme and Bayer Healtheare Announce Detailed Interim Two-Year Alemluzumab in Multiple Sclerosis Data Presented at AAN: Interim Analysis of Phase 2 Comparative Study Showed Significant Results in Favor of Alemtuzumab Versus Rebif®", Issued May 2, 2007, Cambridge, MA and Wayne, NJ.

Genzyme Corporation and Bayer Schering Pharma AG Press Release. "Genzyme and Bayer Schering Pharma AG, Germany Announce Start of Phase 3 Program with Alemtuzumab for Treatment of Multiple Sclerosis", Issued Sep. 26, 2007, Cambridge, MA and Berlin, Germany.

Genzyme Corporation Press Release. "Top-Line Efficacy Data Presented from Phase 2 Trial of Alemtuzumab in Multiple Sclerosis: Three-Year Analysis Demonstrates Robust, Highly Statistically Significant Treatment Effect of Alemtuzumab Compared to Rebif®", Issued Oct. 15, 2007, Cambridge, MA.

Genzyme Corporation and Bayer Healthcare Pharmaceuticals, Inc. Press Release. "Study Results: Multiple Sclerosis Patients Have Significant and Sustained Reduction in Disability and Risk of Relapse on Alemtuzumab Versus Approved Therapy, Rebif®", Issued Oct. 22, 2008, Cambridge, MA and Wayne, NJ.

Genzyme Corporation Press Release. "Genzyme and Bayer Healthcare Enter New Strategic Agreement", Issued Mar. 31, 2009, Cambridge, MA.

Genzyme Corporation Press Release. "Genzyme's Alemtuzumab for Multiple Sclerosis Shows Durable Treatment Benefit in Review of Four-Year Phase 2 Trial Data", Issued Sep. 11, 2009, Cambridge, MA.

University of Cambridge Press Release. "Genzyme Corporation's Generous Benefaction to Enable the Creation of a Key Clinical Academic Post for Multiple Sclerosis, Neuroimmunological Diseases", Issued Mar. 4, 2010, Cambridge, UK.

Genzyme Corporation Press Release. "Significant Percentage of MS Patients Receiving Alemtuzumab in Genzyme's Phase 2 Trial Remain Free of Clinically-Active Disease", Issued Apr. 14, 2010, Cambridge, MA.

Genzyme Corporation Press Release. "Genzyme's Alemtuzumab Shows Sustained Reduction in Relapses and Disability in Five-Year Review of MS Patients from Phase 2 Trial", Issued Oct. 14, 2010, Cambridge, MA.

Hauser, Stephen L., "Multiple Lessons for Multiple Sclerosis", The New England Journal of Medicine, vol. 359(17), pp. 1838-1841 (Oct. 23, 2008).

O'Donnell, Louise, "Safety & Management of CAMPATH Infusion Reactions in MS Patients", Oral Presentation Presented at the *2004 Annual Meeting of the Consortium of Multiple Sclerosis Centers (CMSC)*, Toronto, Ontario, Canada, Jun. 2-6, 2004.

Fox E., et al., "Open-label, single-arm phase II study of high-dose alemtuzumab in patients with active relapsing-remitting multiple sclerosis who have failed licensed beta-interferon therapies," Conference information: 21st Congress of the European-Committee-for-Treatment-and-Research-in-Multiple-Sclerosis/10th Annual Meeting of Rehabilitation in MS Sep. 28-Oct. 1, 2005 Thessaloniki, Greece, Source: Multiple Sclerosis vol. 11 pp. S172-S173 Supplement: Suppl. 1 Published: Sep. 2005.

Fox E., and Mayer L., "Alemtuzumab treatment in relapsing-remitting multiple sclerosis patients who have failed licensed beta-interferon treatment: one-year data," *The 16th Annual Meeting of the European Neurological Society (ENS)*, Lausanne, Switzerland, May 27-31, 2006. Published in *Journal of Nuerology*, 253(Suppl. 2): 59 (2006).

Weinblatt, Michael E., et al., "Campath-1H, A Humanized Monoclonal Antibody, In Refractory Rheumatoid Arthritis," *Arthritis & Rheumatism*, 38(11):1589-1594, (1995).

Weinblatt, Michael E., et al., "Sustained Lymphocyte Suppression After Single Dose Campath®-1H (C-1H) Infusion: A Long Term Follow-Up," *Arthritis & Rheumatism*, 39(9) Supplement: S245 (1996).

Coles, A., et al., "Treatment of Multiple Sclerosis with the Monoclonal Antibody, Campath-1H," 2003 Annual Meeting of the Consortium of Multiple Sclerosis Centers (CMSC), May 28-Jun. 1, 2003, San Diego, CA.

Bloomberg Transcript of Genzyme ECTRIMS Data Investor Conference Call. "Multiple Sclerosis (MS) Trial Phase 2 Result Call", Dated Oct. 14, 2010.

Baidu Encyclopedia, [online] [retrieved on Dec. 20, 2011]. Retrieved from http://baike.baidu.com/view/293304.htm.

Balan et al., "Thyroid Dysfunction Following Anti-Lymphocyte Monoclonal Antibody Treatment of Multiple Sclerosis—

(56) References Cited

OTHER PUBLICATIONS

Scintigraphic Assessment", Journal of Nuclear Medicine, Proceedings of the 45th Annual Meeting, 39(5 Supp.):263P, No. 1156 (1998).
Bartosik-Psujek et al., "Change of Interleukin-4 and Interleukin-12 Levels after Therapy of Multiple Sclerosis Relapse with Methylprednisolone," Neurologia i Neurochirurgia Polska, 39(3):207-212 (2005) (including English abstract).
Bayes et al., "Gateways to clinical trials," Methods & Findings in Experimental & Clinical Pharmacology, 26(1):53-84 (2004).
Boggild, "Rationale and experience with combination therapies in multiple sclerosis," Journal of Neurology, 253:45-51 (2006).
Bonn, "Leukocyte depletion for leukaemia and multiple sclerosis," Molecular Medicine Today, 4(12):508 (1998).
Brochet, "Non-specific immunosuppression in multiple sclerosis," Revue Neurologique (Paris), 154(8-9):629-634 (1998) (English abstract included).
Chofflon, "Mechanisms of action for treatments in multiple sclerosis," BioDrugs, 19(5):299-308 (2005).
Cohen et al., "Treatment of refractory autoimmune diseases with ablative immunotherapy using monoclonal antibodies and/or high dose chemotherapy with hematopoietic stem cell support," Current Pharmaceutical Design, 9(3):279-288 (2003).
Cohen et al., "Treatment of refractory autoimmune diseases with ablative immunotherapy," Autoimmunity Reviews, 3(2):21-29 (2004).
Coles et al., "Disease Activity and the Immune Set in Multiple Sclerosis," Multiple Sclerosis, 4:232-238 (1998).
Coles et al., "Inflammation, demyelination, and axonal degeneration: Three aspects of the pathogenesis of multiple sclerosis revealed by Campath-1H treatment," in Early Indicators, Early Treatments, Neuroprotection in Multiple Sclerosis, O.R. Hommes and G. Comi, editors, 2004, pp. 15-25.
Coles et al., "Campath-1H Treatment of Multiple Sclerosis," Neurologia Croatica,, 52(Supplement 1):12 (2003).
Coles et al., "Campath-1H Treatment of Multiple Sclerosis," Neurology, 60(Supplement 1):A168-A169 (2003).
Compston et al., "Campath-1H Exposes Three Mechanisms Underlying the Natural History of Multiple Sclerosis in the Individual Patient," Journal of Neuroimmunology, 90(1):96 (1998).
Compston, "The Pathogenesis and Basis for Treatment in Multiple Sclerosis," Neurologia Croatica, 52(Supplement 1):13 (2003).
Confavreux et al., "Non-specific immunosuppressants in the treatment of multiple sclerosis," Clinical Neurology and Neurosurgery, 106(3):263-269 (2004).
Confavreux et al., "Accumulation of irreversible disability in multiple sclerosis: from epidemiology to treatment," Clinical Neurology and Neurosurgery, 108(3):327-332 (2006).
Cox et al., "Campath-1H in the Treatment of Patients with Worsening Multiple Sclerosis," Journal of Neurology, Neurosurgery and Psychiatry, 74(3):407 (2003).
Cox et al., "The double-edged sword of treating autoimmunity: insights from therapeutic lymphocyte depletion in the treatment of multiple sclerosis," Journal of Neuroimmunology, 178:212 (2006).
Cox et al., "A Survey of Autoimmunity after Therapeutic Lymphocyte Depletion in the Treatment of Multiple Sclerosis," Journal of Neurology, Neurosurgery and Psychiatry, 77(1):139 (2006).
Cree, "Emerging monoclonal antibody therapies for multiple sclerosis," Neurologist, 12(4):171-178 (2006).
Dumont, "Alemtuzumab (Millennium/ILEX)," Current Opinion in Investigational Drugs, 2(1):139-160 (2001).
Ferrajoli et al., "Alemtuzumab: A novel monoclonal antibody," Expert Opinion on Biological Therapy, 1(6):1059-1065 (2001).
Fox, on behalf of the RENEW Study Group, "Ongoing evaluation of the safety and tolerability of Novantrone® (mitoxantrone) worsening multiple sclerosis: the RENEW study," presented at the 22$^{nd}$ Congress of the European Committee for the Treatment and Research in Multiple Sclerosis (ECTRIMS), Madrid, Spain (2006).

Genzyme Corporation Press Release, "Genzyme's Alemtuzumab for Treatment of Multiple Sclerosis Granted Fast Track Status by the FDA," Issued Jun. 14, 2010, Cambridge, MA.
Genzyme Corporation Press Release, "Sanofi Reports Positive Top-Line Results from First Phase 3 Study of Alemtuzumab (Lemtrada™ (*)) in Multiple Sclerosis," Issued Jul. 11, 2011, Business Wire [online] [retrieved on Feb. 25, 2013]. Retrieved from http://www.businesswire.com/news/home/20110710005114/en/Sanofi-Reports-Positive-Top-Line-Results-Phase-3.
Genzyme Corporation Press Release, "Genzyme Announces Successful Phase III Results for Alemtuzumab (LEMTRADA™ *) in Multiple Sclerosis," Issued Nov. 14, 2011, Business Wire [online] [retrieved on Feb. 12, 2013]. Retrieved from http://www.businesswire.com/news/home/20111113005072/en/Genzyme-Announces-Successful-Phase-III-Results-Alemtuzumab.
"Genzyme Reports Interim Results from Trial of Campath(R) for Multiple Sclerosis", Sep. 14, 2006, pp. 6-7 in "Campath", The Multiple Sclerosis Resource Centre, pp. 1-11, [online], [retrieved on Dec. 4, 2007]. Retrieved from http://www.msrc.co.uk/index.cfm?fuseaction=show&pageid=1307.
Hale et al., "Clinical trials with Campath-1H and other monoclonal antibodies," Biochemical Society Transactions, 23(4):1057-1063 (1995).
Hirst et al., "Is Campath-1H an effective rescue treatment in patients with aggressive relapsing-remitting multiple sclerosis?" Multiple Sclerosis, 12:S217-S218 (2006).
Hutton, on behalf of the CAMMS223 Study Group, "Care-MS$^{SM}$ II Trial (Comparison of Alemtuzumab and Rebif® Efficacy in Multiple Sclerosis): Updated Design of a Phase 3, Open-Label, Rater-Blinded Study of Alemtuzumab in Patients with Multiple Sclerosis Who Have Relapsed on Therapy," The 19th Meeting of the European Neurological Society (ENS), Milan, Italy, (Jun. 20-24, 2009).
Jones et al., "Increased Apoptotic Elimination of Activated T-cells after Campath-1H Treatment of Multiple Sclerosis," Immunology, 116(Supplement 1):41 (2005).
Jones et al., "Increased apoptotic elimination of activated T-cells following Campath-1H as a treatment of multiple sclerosis," Journal of Neuroimmunology, 178:54-55 (2006).
Jones et al., "Neurotrophin Secretion after Lymphodepletion with Campath-1H in Multiple Sclerosis," Journal of Neuroimmunology, 178:211-212 (2006).
Moreau et al., "Campath-1H in Multiple Sclerosis," Multiple Sclerosis, 1:357-365 (1996).
O'Donnell, "Safety & Management of CAMPATH Infusion Reactions in MS Patients," Draft slides for oral presentation at 2004 Annual Meeting of the Consortium of Multiple Sclerosis Centers (CMSC), Toronto, Ontario, Canada, Jun. 2-6, 2004.
Paolillo et al., "Quantitative MRI in Patients with Secondary Progressive MS Treated with Monoclonal Antibody Campath 1H," Neurology, 53(4):751-757 (1999).
Polman et al., "New and emerging treatment options for multiple sclerosis," Lancet Neurology, 2(9):563-566 (2003).
Reiff, "A review of Campath in autoimmune disease: biologic therapy in the gray zone between immunosuppression and immunoablation," Hematology, 10(2):79-93 (2005).
Rioux, "Campath-1H (Cambridge University)," IDrugs 2(2):153-167 (1999).
Rioux, "Campath Cambridge University," Current Opinion in Anti-Inflammatory Immunomodulatory Investigational Drugs, 1(4):384-402 (1999).
Rioux, "Campath-1H (Cambridge University UK)," Current Opinion in Oncologic, Endocrine & Metabolic Investigational Drugs, 1(3):300-318 (1999).
Rizvi et al., "Other therapy options and future strategies for treating patients with multiple sclerosis," Neurology, 63(12 Suppl 6):S47-54 (2004).
Robertson et al., "Lymphocyte Homeostasis and Regulatory Cells in Multiple Sclerosis," Journal of Neuroimmunology, 178:211 (2006).
Rovaris et al., "Interventions for the prevention of brain atrophy in multiple sclerosis: current status," CNS Drugs, 17(8):563-575 (2003).

(56) References Cited

OTHER PUBLICATIONS

Schmidt et al., "Current treatment of multiple sclerosis. Treatment with anti-T cell antibodies (CD3, CD4, CD52)," Nervenarzt, 67(2):170-176 (1996) (English abstract included).
Smirnova et al., "Klinikoimmunologicheskie Proyavleniya i Naruzheniya Metabolisma Vnutrikletochnykh Fermentov Lymfotsytov u Bolnykh Khronicheskym Limfoletkosom," Sibirskiy Onkologicheskiy Zhurnal, 2(22):15-21 (2007) (including English abstract).
Smith et al., "Recent developments in drug therapy for multiple sclerosis," Multiple Sclerosis, 5(2):110-120 (1999).
Svendsen et al., "Pain in patients with multiple sclerosis: a population-based study," Archives of Neurology, 60(8):1089-1094 (2003).
Thompson et al., "B Lymphocyte Homeostasis in Multiple Sclerosis Patients Treated with CAMPATH-1H," Immunology, 116(Supplement 1):42 (2005).
Thompson et al., "B Cell Homeostasis and the Role of B Cell Activating Factor in Patients with Multiple Sclerosis Treated with Campath-1H," Journal of Neuroimmunology, 178:212 (2006).
"Uncertainty Dogs Campath for MS", Feb. 14, 2006, pp. 7-8 in "Campath", The Multiple Sclerosis Resource Centre, pp. 1-11, [online], [retrieved on Dec. 4, 2007]. Retrieved from http://www.msrc.co.uk/index.cfm?fuseaction=show&pageid=1307.
United States Patent and Trademark Office, "Non-Final Office Action," issued in U.S. Appl. No. 13/724,958 (Mar. 5, 2013).
Wiendl et al., "Multiple sclerosis: potential therapeutic options and update of ongoing clinical trials," Nervenarzt, 75(6):536-552 (2004) (English abstract included).
Yu et al., "Therapeutic Advances of the Multiple Sclerosis," [online] [retrieved on Dec. 20, 2011]. Retrieved from http://journal.9med.net/html/qikan/zgyx/zhxdzyxzz/2007633/lz/20080831063955810_315212.html (English abstract included).
Schuster L., "MS: Simvastatin and Alemtuzumab Appear Promising, But Are Not Ready for Use," *Neurology Today*, 3(8):44-45 (2003).
Vargas, M.T., et al., "Antithyroid Microsomal Autoantibodies and HLA-DR5 are Associated with Postpartum Thyroid Dysfunction: Evidence Supporting an Autoimmune Pathogenesis," *J. of Clin. Endocrinol. and Metabol.*, 67(2):327-333 (1988).
Non-published U.S. Appl. No. 12/526,129, filing date (371(c)) Jan. 29, 2010 (U.S. National of PCT/US2008/002047, filed Feb. 15, 2008).

\* cited by examiner

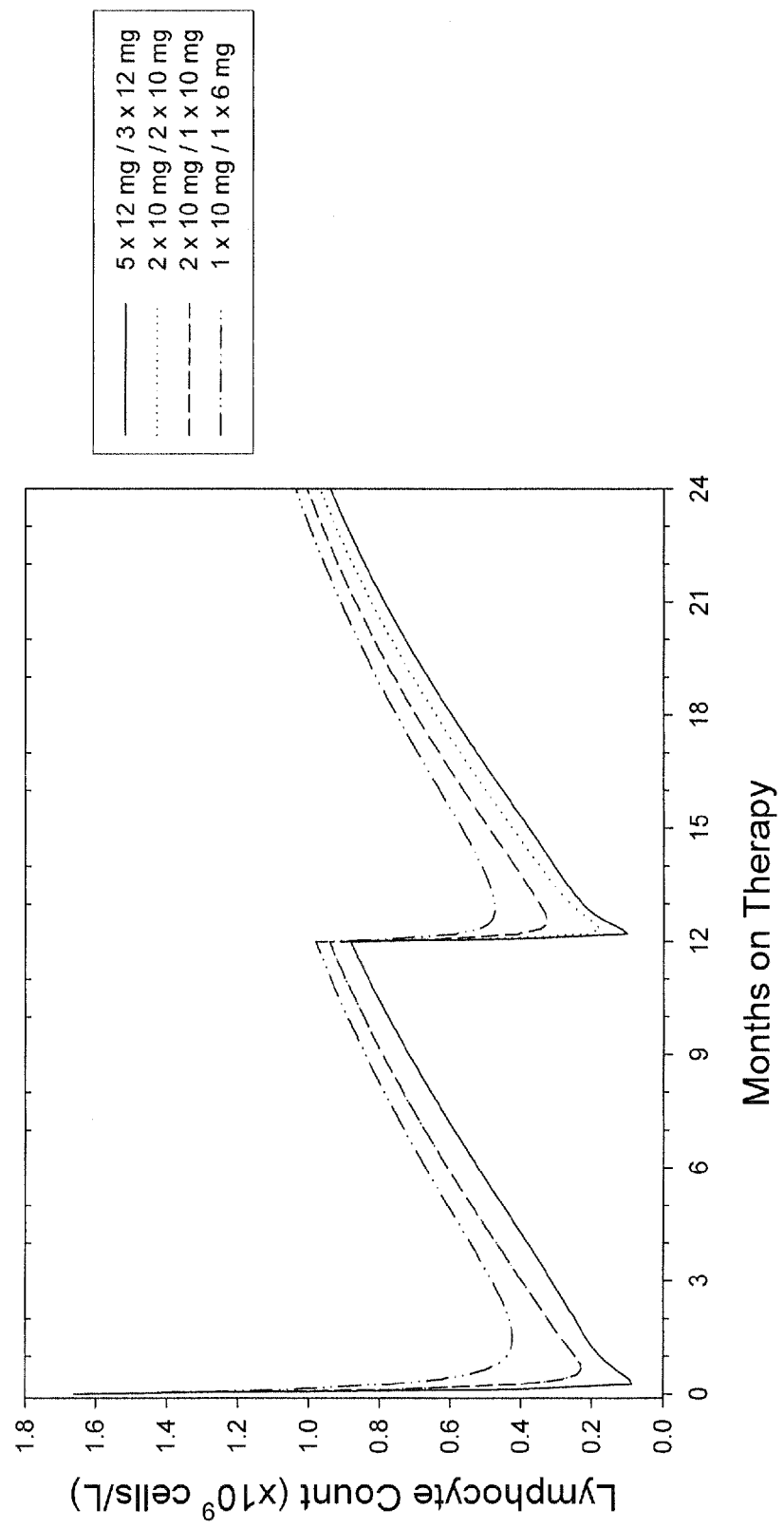

TREATMENT OF MULTIPLE SCLEROSIS (MS)

RELATED APPLICATION(S)

This application claims the benefit of U.S. Provisional Application No. 60/844,251, filed on Sep. 13, 2006. The entire teachings of the above application(s) are incorporated herein by reference.

BACKGROUND OF THE INVENTION

Multiple sclerosis (MS) is an inflammatory demyelinating disease of the central nervous system that affects as many as 2.5 million people worldwide. The pathogenesis of MS remains poorly understood but is believed to arise from the interplay of polygenic inherited susceptibility and an unidentified environmental agent(s). It is approximately twice as common among women as men. Worldwide, its prevalence varies geographically and, within the same country, between different racial groups. Prevalence is highest amongst Caucasians in countries distant from the Equator, for instance Scotland and Scandinavia. Peak incidence is within the third and fourth decades; it is extremely uncommon to make a new diagnosis in patients over the age of 60 years [National Multiple Sclerosis Society, General Information, Just the Facts: 2000-2001. National Multiple Sclerosis Society; 2001.].

Campath-1H (alemtuzumab) is a recombinant DNA-derived humanized monoclonal antibody that is directed against the 21-28 kD cell surface glycoprotein, CD52. CD52 is an abundant molecule (approximately $5\times10^5$ antibody binding sites per cell) present on at least 95% of all human peripheral blood lymphocytes and monocytes/macrophages [Hale G. et al., The CAMPATH-1 antigen (CD52). *Tissue Antigens* 1990; 35:118-127].

Campath-1H is disclosed in U.S. Pat. No. 5,846,534, wherein a humanized antibody which binds effectively to the antigen CD52 as well as a method of treating a human patient having a lymphoid malignancy with such an antibody is described. Procedures for preparation and testing of such an antibody are disclosed.

Campath-1H (alemtuzumab, Campath® or MabCampath®) is approved for the treatment of B-cell chronic lymphocytic leukaemia (B-CLL) in patients who have been treated with alkylating agents and who have failed fludarabine therapy. As labelled for treatment of CLL, Campath therapy is initiated at a dose of 3 mg administered as a 2 hour i.v. infusion daily. When the Campath 3 mg daily dose is tolerated, the daily dose is escalated to 10 mg and continued until tolerated. When the mg dose is tolerated, the maintenance dose of Campath 30 mg/day is administered three times per week on alternate days (e.g., Monday, Wednesday, and Friday) for up to 12 weeks (see Campath® package insert).

Clinical studies have shown that the Campath-1H antibodies are also active in a variety of other diseases including graft-versus-host disease, organ transplant rejection, rheumatoid arthritis, and other autoimmune diseases, as well as in non-Hodgkin's lymphoma and leukemias [Hale G, Waldmann H. From laboratory to clinic: The story of Campath-1H in antibodies in the clinic. In: George A J T, Ureli C, ed. Methods in Molecular Medicine. Diagnostic and Therapeutic Antibodies. NJ: Humana Press; 2000; 40:319-323].

Hale and Waldmann were the first to disclose the use of Campath-1H in multiple sclerosis. In U.S. Pat. No. 6,120,766, Hale and Waldmann claim a method for the treatment of multiple sclerosis in a human subject which comprises administering an effective amount of Campath-1H and an effective amount of a steroid (e.g. hydrocortisone or methylprednisolone). In that patent, they describe a 43 year old female with chronic progressive MS who had been treated with high doses of i.v. methylprednisolone (second course: 500 mg per day over 5 days) with limited improvement. The patient received 10 doses of Campath-1H over 12 days (2 mg/day for five days, 2 days rest, then 10 mg/day for five days). Fever and headache were reported as adverse events during administration of the first 2 mg and 10 mg doses. One and two months after Campath-1H administration the Kurtzke neurological status of the patient had improved and the improvement was maintained 18 months after the treatment.

Since then, Campath-1H has been used in a variety of clinical studies in patients with primary progressive MS and secondary progressive MS (PPMS and SPMS, respectively). For example, in 1994, T. Moreau et al. reported the treatment of six SPMS patients and 1 PPMS patient with Campath 1H at 12 mg/day for 10 days (*Lancet* (1994), 344:298-301).

In 1996, T. Moreau et al. described the treatment of twelve SPMS and one PPMS patient with Campath-1H using doses of 2 mg/day for 5 days and then 10 mg/day for 5 days, or using 12 mg day for 10 days, or using 20 mg/day for 5 days (*Brain* (1996), 119:225-237). They reported that serum cytokine release, coinciding with the first infusion of Campath-1H and the induction of lymphopaenia, is associated with transient symptomatic deterioration and altered conduction through previously affected CNS pathways.

In 1999, Coles et al. reported the treatment of 29 patients with SPMS using a dose of 20 mg/day for 5 days (*Ann. Neurol.* (1999), 46:296-304). They observed a transient reversal of previous or current symptoms during the first dose of Campath-1H. About half the patients experienced progressive disability and increasing brain atrophy, attributable on the basis of MRI spectroscopy to axonal degeneration. Later in 1999, Coles et al. reported on the long term follow-up of 27 of the patients reported in a previous study (*Lancet* (1999), 354:1691-95). One third of the patients had developed antibodies against the thyrotropin receptor and carbimazole-responsive autoimmune hyperthyroidism (i.e., Graves' disease).

In 2003, Coles et al. reported that of the 36 SPMS patients who had received Campath 1H since 1991, their relapse rate remained suppressed during a mean of 7 years of follow-up but their disability had continued to progress. In addition, one third (⅓) of the patients had developed Graves' disease (*Neurology* 60 Mar. 2003 (Suppl. 1). They also reported the treatment of 22 patients with relapsing remitting MS (RRMS). A later report of these 22 RRMS patients confirmed that they had received a dose of 20 mg/day for 5 days and elective re-treatment was offered after 12-18 months at 20 mg/day for 3 days (*Clinical Neurology and Neurosurgery* (2004), 106:270-274). The principal adverse event was Graves' disease which developed within 5-21 months of the first treatment (14 patients) and two years after the second cycle (1 patient) in a total of 15 of the 57 patients (27%) (one patient had Grave's disease before receiving Campath-1H).

In 2004, O'Donnell et al. reported at the Art and Science of MS Meeting held in Toronto on an ongoing trial comparing two dose levels of Campath-1H to interferon beta-1a (Rebif®, Ares-Serono) in patients with early active RRMS. In this trial, (CAMMS223), Campath-1H was administered at a dose of 12 mg/day (low dose) or 24 mg/day (high dose)

for five days. The interferon beta-1a patients received three s.c. injections per week as indicated in the product label (Rebif®).

Interim results from the CAMMS223 trial were announced by Genzyme Corporation and Schering AG Germany on Sep. 16, 2005. These results were derived from a pre-specified efficacy and safety interim analysis conducted after one year of treatment for all patients in the planned three year trial. Patients were treated with Campath-1H at low (12 mg/day) or high (24 mg/day) doses administered over five days in once a year intravenous infusion regimens, or interferon beta-1a administered three times per week as indicated in its product label. At 12 months, patients on Campath-1H received a dose of 12 or 24 mg/day for three days. Patients taking Campath in both the high and low doses experienced at least a 75% reduction in the risk for relapse after at least one year of follow up when compared to patients treated with interferon beta-1a. The Campath patients additionally experienced at least a 60% reduction in the risk for progression of clinical significant disability compared to Rebif®. However, three cases of severe idiopathic thrombocytopenic purpura (ITP) were reported (two in the high dose group and one in the low dose group).

Also in 2005, Fox et al. reported during ECTRIMS on a study of high-dose Campath in 45 patients with active RRMS who had failed licensed IFN-beta therapies. Campath was given at 24 mg/day for 5 days and then repeated after one year at 24 mg/day for 3 days. One drug-related serious adverse event occurred (neutropenia and pneumonia) and abnormal thyroid values were found in several patients.

In summary, administration of Campath-1H at to patients with MS has shown efficacy in treating the disease, but such administration has also been associated with adverse events, which may include infectious and auto-immune complications. Thus, there remains a need for Campath-1H regimens which result in significant efficacy in this patient population (i.e. reduction in risk for relapse and/or reduction in risk for progression of clinical significant disability) while having an acceptable safety profile.

SUMMARY OF THE INVENTION

The present invention relates to a method for the treatment of multiple sclerosis (MS) with Campath-1H, with significant efficacy and a favourable safety profile which offers an acceptable benefit/risk ratio. It also relates to the use of Campath-1H for the production of a medicament for the treatment of multiple sclerosis (MS).

The invention relates to a method for the treatment of multiple sclerosis (MS) in a patient, comprising administration of a first cycle of Campath-1H followed by at least one further cycle of Campath-1H, in which each treatment cycle comprises 1-5 doses which are applied on consecutive days, wherein the daily dose is >0 and ≤12 mg, and wherein each treatment cycle is separated from the next cycle by at least 1-24 months.

In some embodiments, patients are re-treated on a fixed time course, e.g., at 6, 12, 18 or 24 months after the first treatment. In other embodiments, patients are re-treated only once evidence of renewed MS activity has been observed.

In some embodiments, re-treatment occurs at the same dose and duration as the initial dose. In other embodiments, re-treatment occurs at the same dose for a different duration, or at a different dose for the same duration, as the initial cycle of treatment.

The invention also relates to a method for the treatment of multiple sclerosis in a patient, comprising administration of Campath-1H at a dose of less than 12 mg/day for a period of 1-5 days.

The invention also relates to the use of Campath-1H for the production of a medicament to be administered according to the methods described herein.

The methods and uses of this invention are applicable to patients with relapsing MS as well as patients with progressive MS.

The foregoing summary and the following detailed description are exemplary and explanatory only and are not restrictive of the invention as claimed.

BRIEF DESCRIPTION OF THE FIGURES

FIG. 3 presents a line plot of selected dosing regimens from FIG. 1. Data for the two 10 mg doses administered during the first cycle are overlaid over each other and not discernible from each other.

DETAILED DESCRIPTION OF THE INVENTION

Figure 1:
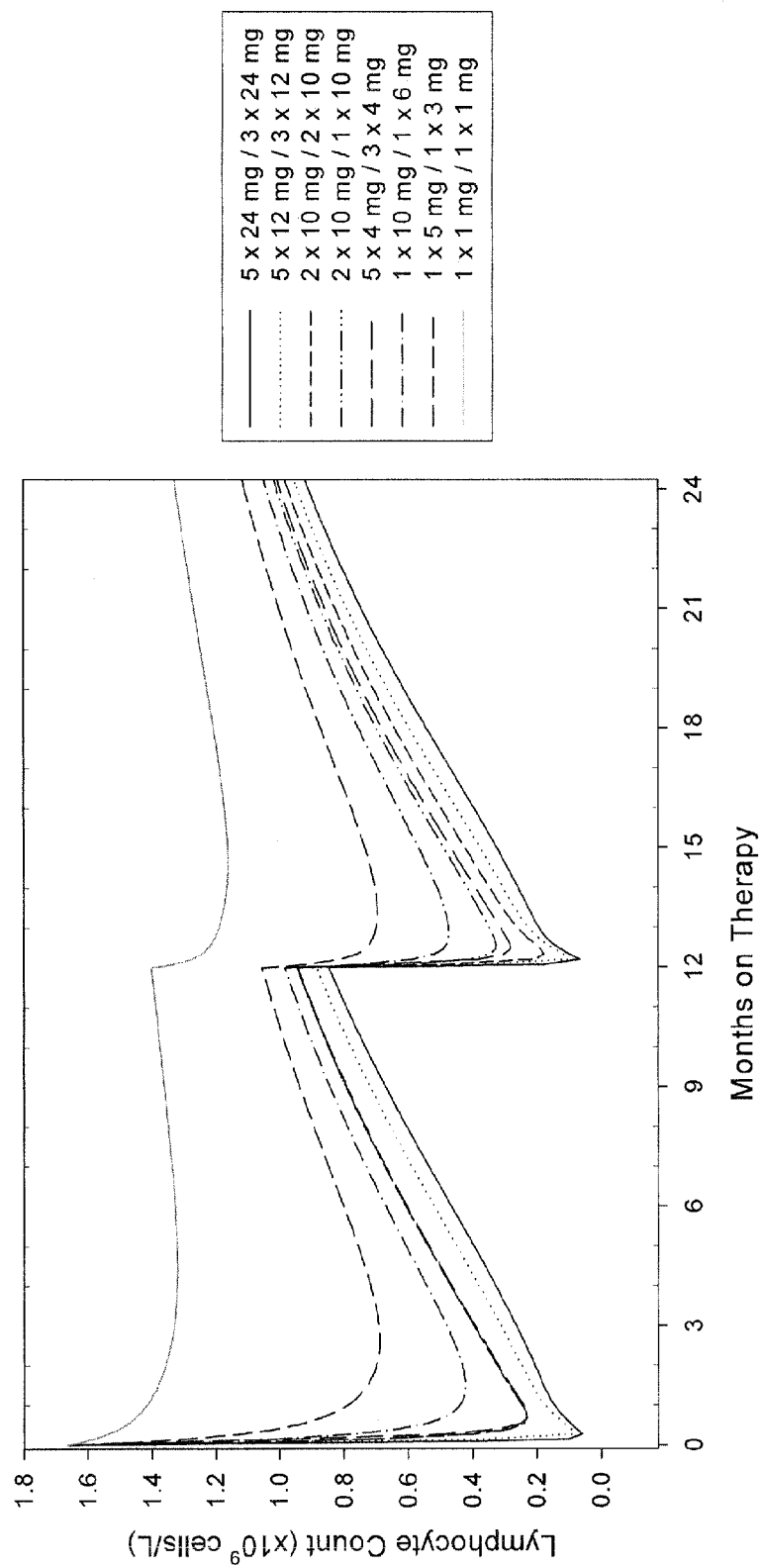
FIG. 1 presents a line plot of the simulated dosing regimens over a 24 month period. In the legend, the first set of numbers indicate the number of days by the daily dose. For example, 5×12 mg is 5 days of 12 mg infused over a 4 hour period. The second set of numbers are the retreatment doses on Month 12.
Figure 2:
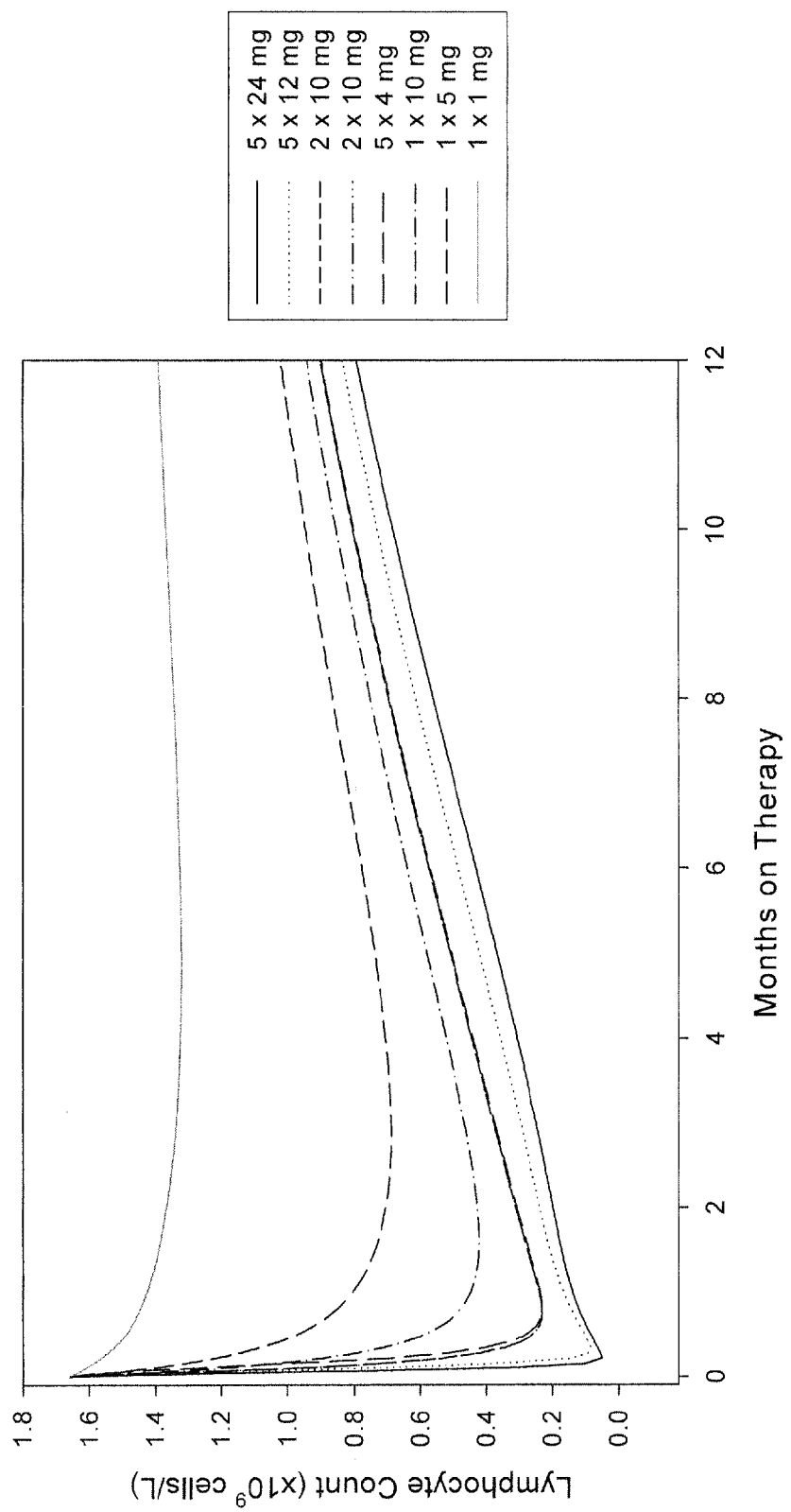
FIG. 2 presents a line plot of the simulated dosing regimens over a 12 month period.

As used herein, the term "Campath-1H" refers to the monoclonal antibody of the same name disclosed in U.S. Pat. No. 5,846,534 (also known as alemtuzumab) as well as human or humanized monoclonal antibodies having the same CDR sequences as Campath-1H.

In one aspect, the invention relates to the use of Campath-1H for the production of a medicament for the treatment of relapsing MS patients, characterised in that the Campath-1H is administered at a dose of less than 12 mg/day for a period of 1-5 consecutive days.

In another aspect, the invention relates to a method for treating relapsing MS patients which comprises the administration of Campath-1H at a dose of less than 12 mg/day for period of 1-5 consecutive days.

In another aspect, the invention relates to a method for treating MS patients which comprises the administration of Campath-1H at a dose of less than 12 mg/day for a period of 1-5 consecutive days and then re-treating such patients using a treatment regimen equal to or less than the original regimen in either dose (mg/day) and/or duration (number of days).

In certain embodiments, the Campath-1H is administered at a dose of 11, 10, 9, 8, 7, 6, 5 or 4 mg/day for a period of 5 days. In other embodiments, the Campath is administered at a dose of 11, 10, 9, 8, 7, 6, 5 or 4 mg/day for periods of 2 or 3 or 4 days.

In another aspect, the invention relates to a method for treatment of MS, which comprises the cyclic application of Campath-1H in daily doses of up to 12 mg/day over a period of 1-5 days with each treatment cycle being separated from the prior cycle (i.e. Campath-1H dosing) by at least one month. In certain embodiments, the Campath-1H is administered at a dose of 2-10 mg per day.

In various embodiments, daily doses can remain the same for each cycle of treatment or may differ for the different treatment cycles (e.g. 10 mg/d for first cycle, 5 mg/d for subsequent cycles). Also contemplated by the inventors are daily doses that vary within one treatment cycle e.g., by escalation (e.g. 8 mg on first day, 10 mg on second day and 12 mg on third day and so on), or vice-versa.

The number of consecutive days of treatment (i.e. dosing) per cycle is normally 1-5. In certain embodiments, a cycle is 1-3 days. The number of dosing days can remain the same for each cycle or may differ for the different treatment cycles (e.g. 3 days for first cycle, 2 days for subsequent cycles). Less dosing days per cycle is expected to result in improved patient convenience/acceptance and reduced treatment cost.

In another aspect, the invention relates to the use of Campath-1H for the production of a medicament for the treatment of MS, which comprises the cyclic application of Campath-1H in daily doses of up to 12 mg/day over a period of 1-5 days with each treatment cycle being separated from the prior cycle (i.e. Campath-1H dosing) by at least 1 month.

In some embodiments directed to cyclic application, the consecutive treatment cycles are separated by at least 3 or 6 months. In other embodiments, they are separated by at least 18 or 24 months. In certain embodiments, the number of consecutive treatment cycles is not limited so that lifelong treatment is potentially possible. In other embodiments, the number of treatment cycles is limited to 2-10 or 2-5 cycles.

In some embodiments, re-treatment occurs on a fixed time course, e.g., at 6, 12, 18 or 24 months after initial treatment.

In another aspect of the invention, re-treatment (i.e. application of an additional treatment cycle of 1-5 consecutive daily doses of ≤12 mg) only occurs once evidence of renewed MS activity in the respective patient is observed. This treatment regimen is referred to herein as "re-treatment as needed."

Evidence of renewed MS activity may be determined based on the professional judgement of the treating clinician, using any means that may be available to such clinician.

A variety of techniques are currently available to clinicians to diagnose renewed MS activity including, without limitation, by clinical means (relapse or progression of neurological disability) or by magnetic resonance imaging (MRI) of the brain or spinal cord. As is well understood by medical practitioners, disease activity detected via MRI may be indicated by the occurrence of new cerebral or spinal lesions on T1 (enhanced or non-enhanced)- or T2 weighted images or by the increase of the volume of such lesions. As diagnostic methods for MS are continually evolving, it is anticipated there may be additional methods in the future that will detect renewed MS activity (e.g. magnetization transfer ratio or MR-spectroscopy). The particular diagnostic method used to detect renewed MS activity is not a limitation of the claimed invention.

In certain embodiments, repeated MRIs are performed in fixed intervals after a treatment cycle in order to determine whether re-treatment of any given patient is necessary and the optimal time point for re-treatment of such patient. In general, it is desirable for re-treatment to occur before the disease re-manifests clinically.

This "re-treatment as needed" strategy is expected to maximize the benefit/risk ratio of the treatment regimens disclosed herein by potentially avoiding unnecessary drug exposure in patients with sustained MS suppression.

In embodiments which include re-treatment, it may be immediately initiated prior to or subsequent to cessation of any symptomatic treatment (e.g. steroids) which may have been administered for the acute relapse (i.e. no fixed interval (time period) between subsequent treatment cycles).

In certain embodiments, re-treatment upon renewed MS activity is only performed if at least 3-24 months have passed since the last treatment cycle.

In another aspect, the invention relates to the use of Campath-1H for the production of a medicament for the treatment of MS, which comprises the cyclic application of Campath-1H in daily doses of up to 12 mg/day over a period of 1-5 days, wherein re-treatment only occurs once evidence of renewed MS activity in the respective patient is observed.

All of the methods and uses of the invention are applicable to both relapsing as well as progressive forms of multiple sclerosis (MS). Patients with relapsing forms of MS are currently expected to respond more favourably than those with progressive forms.

MS patients amenable to treatment may be patients who were originally treated with other drug(s) (e.g., treatment failures) or patients who have not received prior MS therapy (i.e. treatment (drug) naïve patients).

In the methods and uses of the invention, Campath-1H may be administered via any acceptable route including, without limitation, via parenteral administration (e.g. intravenous, subcutaneous, intramuscular, intraperitoneal, nasal, pulmonary). In certain embodiments, Campath-1H is administered intravenously (i.v.) or used for the production of a medicament to be administered intravenously.

In cases where premedication is desired, any drugs known to those skilled in the art to be effective for such purpose, such as for example steroids (e.g. methylprednisolone), acetaminophen and antihistamines (e.g. diphenhydramine) may be applied before, during or after infusion to manage infusion related side effects. In certain embodiments, only low doses of such drugs are utilized during the first 1-3 days of application during each treatment cycle. In other embodiments, no concomitant medication is administered.

Campath-1H treatment according to the methods of the invention, and uses of Campath-1H for the production of medicaments according to the invention, potentially lead to a low rate of (serious) adverse events. Consequently MS treatment regimens according to the method of the invention are expected to result in an acceptable benefit/risk ratio.

According to the instant invention, Campath-1H is administered, or used for the production of a medicament to be administered, in a suitable pharmaceutical formulation containing appropriate excipients as known to those skilled in the art. The current Campath® (MabCampath®) formulation represents one example of such a suitable product (see Campath® package insert). In addition to a solution, Campath-1H may also be formulated as a freeze-dried product which is reconstituted prior to use.

The formulation is preferably provided in vials or plastic bags (mainly for i.v. use) but other standard containers as known to those skilled in the art can also be used depending on the route of application (e.g. pre-filled syringes for s.c. application or spray (aerosol) containers for nasal and pulmonary use).

Thus, the advantages of the invention are:
Maximization of benefit/risk ratio and/or
Minimization of drug exposure and/or
Improved patient convenience/acceptance and/or
Reduction of infusion related side effects and/or
Reduction of the rate of opportunistic infections and/or
Reduction of thyroid abnormalities (inc. Graves' disease) and/or
Reduction of autoimmune hematological complications (e.g. thrombocytopenia) and/or
Reduction of other (serious) adverse events and/or
Minimization of antibody formation to Campath-1H In certain embodiments of the invention two initial fixed treatment cycles which are separated by 1-24 months are followed by a third or subsequent treatment cycle(s) only upon evidence of renewed MS activity (i.e. "re-treatment as needed"). Thus the third and subsequent treatment cycle(s) may be initiated immediately prior to or subsequent to cessation of any symptomatic treatment (e.g. steroids) which may have been administered for the acute relapse (i.e. no fixed interval (time period) between subsequent treatment cycles). Alternatively, re-treatment upon renewed MS activity is only performed if at least 3-24 months have passed since the second (previous) treatment cycle.

In one embodiment of the invention, Campath-1H is initially administered, or used for the production of a medicament to be initially administered (Month 0) at a dose of 10 mg/day for two consecutive days followed by a second fixed treatment cycle of 10 mg/day for two consecutive days at Month 12. Subsequent re-treatment is then only conducted on a re-treatment as needed basis with one or more additional cycles of 10 mg/day for two days.

In another embodiment of the invention, Campath-1H is initially administered, or used for the production of a medicament to be initially administered (Month 0) at a dose of 12 mg/day for five consecutive days followed by a second fixed treatment cycle of 12 mg/day for three consecutive days at Month 12. Subsequent re-treatment, is then only conducted on a re-treatment as needed basis with one or more additional cycles of 12 mg/day for three days.

It is anticipated that these treatment and use regimens will result in a sustained depletion of lymphocytes and a commensurate degree of clinical benefit while affording safety advantages over the regimens previously used in this patient population.

Without being bound by theory, these treatment and use regimens have been developed based in part on an analysis of Campath-1H pharmacokinetics and pharmacodynamics in patients enrolled in the CAMMS223 clinical trial. A variety of pharmacokinetic and pharmacodynamic models were developed for the purpose of this analysis. Model selection was based on physiological and pharmacological rationale and the principle of parsimony—simpler models were chosen over more complex models when statistically justified. First, exploratory data analysis was undertaken to examine the basic structure of the concentration-time data and to identify any outliers. Second, various structural models, such as the 2-compartment model, were developed without covariates. Once the basic structural model was identified, covariates were included in the model to see whether their inclusion improved the goodness of fit. Once the final pharmacokinetic model was identified, these parameters were fixed and the pharmacodynamic model was developed. Only one model type was examined, an indirect response model, which has been shown to be a good model for biomarkers such as hematologic indices. Once the final pharmacokinetic-pharmacodynamic model was identified, the parameters were fixed and deterministic simulations were done to examine the effect of alternate dosing strategies on lymphocyte counts.

The following dosing regimens/uses were examined:
1. 5 days at 24 mg followed by yearly re-treatment/use of 3 days at 24 mg;
2. 5 days at 12 mg followed by yearly re-treatment/use of 3 days at 12 mg;
3. 2 days at 10 mg followed by yearly re-treatment/use of 2 days at 10 mg;
4. 2 days at 10 mg followed by yearly re-treatment/use of 1 day at 10 mg;
5. 5 days at 4 mg followed by yearly re-treatment/use of 3 days at 4 mg;
6. 1 day at 10 mg followed by yearly re-treatment/use of 1 day at 6 mg;
7. 1 day at 5 mg followed by yearly re-treatment/use of 1 days at 3 mg; and
8. 1 day at 1 mg followed by yearly re-treatment/use of 1 day at 1 mg.

These regimens were coded as day×dose for simplicity. So, for example, 5 daily doses of 12 mg would be coded as 5×12 mg, a single dose of 10 mg would be coded as 1×10 mg, etc.

The pharmacokinetic and pharmacodynamic modeling showed that Campath-1H is an extremely potent depleter of lymphocytes. A single 5 mg dose can decrease lymphocytes by ~50% with a nadir occurring about 10 weeks after the dose. Further, the modeling showed that increasing dose resulted in greater lymphocyte depletion, with almost complete lymphocyte depletion seen with the 5×12 mg treatment group. One specific result of this analysis is the recognition that Campath-1H treatment delivered in a cycle of 10 mg/day for two days with re-treatment at 12 months with 10 mg/day for 2 days (i.e., the 20/20 mg regimen) is predicted to lead to a sustained lymphocyte depletion that is only modestly less than with higher doses. Given that the mechanism of action of Campath-1H is presumed to be due to immune suppression, it is anticipated that a modest reduction in lymphopenia will only be associated with a comparably modest reduction in efficacy. Thus, the 20/20 mg regimen is expected to result in a moderately lesser degree of lymphocyte depletion compared with the regimens previously studied.

A lower Campath-1H dosage delivered with fewer infusions is expected to trigger fewer acute infusion reactions and limit the potential for adverse events associated with intravenous (IV) injections in general. In view of the known immune-suppressing effects of Campath-1H, reduction in the administered dose may also result in a lower risk of infectious complications. The relative risk for autoimmune complications is also predicted to be lower.

The following examples demonstrate the feasibility of the invention, without restricting the invention only to these examples.

Example 1

An open, rater blinded, randomized, multicenter trial in treatment naïve patients with early active relapsing-remitting multiple sclerosis is performed. The first treatment cycle of Campath-1H consists of 5 daily doses of 12 mg at Month 0. The second (fixed) treatment cycle consists of 3 daily doses of 12 mg at Month 12. Subsequently, re-treatment of patients with 3 daily doses of 12 mg Campath-1H only occurs once evidence of renewed MS activity is observed in the respective patient. Thus, the third and subsequent cycles are administered only if the patients have evidence of renewed MS activity, in this example defined as at least 1 documented clinical relapse or presentation of at least 3 new MRI lesions (total) compared to the MRI following the prior Campath-1H treatment (i.e. "re-treatment as needed" regimen). If these criteria are fulfilled, the patient may be immediately retreated.

If a Campath-1H patient has received steroids for symptomatic treatment of a relapse within 2-8 weeks prior to a scheduled/planned alemtuzumab infusion, the infusion and pre-medication with steroids may be deferred until 2-8 weeks after steroid dosing for treatment of the relapse. Steroid pretreatment is typically administered on the first three days of the Campath-1H infusion to avoid/minimize infusion related side effects. Consecutive treatment cycles will follow the same "re-treatment as needed" rules as described above.

The patients may receive pre-treatment with 1 g i.v. methylprednisolone over 1 hour on the first 3 days of each treatment cycle in order to ameliorate any cytokine release syndrome.

Example 2

MS patients are treated as set forth above, except that the first treatment cycle of Campath-1H consists of 2 daily doses of 10 mg at Month 0 and the second treatment cycle consists of two daily doses of 10 mg at Month 12. Subsequently re-treatment of patients with 2 daily doses of 10 mg Campath-1H only occurs once evidence of renewed MS activity is observed as described in Example 1 ("re-treatment as needed").

Example 3

MS patients are treated using the same treatment regimens as outlined in Examples 1 or 2, except that the second and subsequent re-treatments are on a re-treatment as needed basis provided that at least 6 months have passed since the prior Campath-1H treatment cycle (dosing period).

Example 4

MS patients are treated using the same treatment regimen as outlined in Example 3, however the patients are re-treated at any time after the initial (prior) Campath-1H treatment cycle (dosing period) if evidence of renewed MS activity has been observed and if the respective patient has not received steroids for symptomatic treatment of a relapse within 2-8 weeks prior to the planned Campath-1H cycle. If a patient has received steroids within 2-8 weeks prior to a planned Campath-1H cycle, then re-treatment is started 2-8 weeks after completion of the steroid treatment.

Example 5

MS patients are treated with two treatment cycles of Campath-1H using dosing regimens as outlined in Examples 1 or 2. However, subsequent to the second cycle at Month 12, re-treatment occurs in 18 months intervals irrespective of renewed disease activity (fixed re-treatment).

All publications, including patents, cited in this disclosure are incorporated by reference in their entirety.

What is claimed is:

1. A method of treating multiple sclerosis (MS) in a patient with a single MS immunotherapeutic consisting of an anti-CD52 antibody, the method comprising:
    administering the anti-CD52 antibody to the patient at 1-12 mg/day for 1-5 days in an initial treatment cycle, and
    at least 3 months after the initial treatment cycle, administering the anti-CD52 antibody to the patient at 1-12 mg/day for 1-5 days in a second treatment cycle.
2. The method of claim 1, wherein the anti-CD52 antibody is administered to the patient at 12 mg/day in the initial treatment cycle and in the second treatment cycle.
3. The method of claim 1 or 2, wherein the anti-CD52 antibody is administered to the patient for five consecutive days in the initial treatment cycle and three consecutive days in the second treatment cycle.
4. The method of claim 1, wherein the period of time between the initial treatment cycle and the second treatment cycle is at least 12 months.
5. The method of claim 1, wherein the patient has no renewed MS activity for at least 12 months after the second treatment cycle.
6. The method of claim 1, wherein the 1-12 mg of the anti-CD52 antibody for each treatment day is administered to the patient via intravenous infusion.
7. The method of claim 1, wherein the patient is pre-medicated with a steroid immediately prior to the anti-CD52 antibody administration on the first three days of each treatment cycle.
8. The method of claim 7, wherein the steroid is methylprednisolone.
9. The method of claim 1, wherein the anti-CD52 antibody is administered to the patient at less than 12 mg/day in the initial treatment cycle and in the second treatment cycle.
10. The method of claim 1, wherein the patient is treated with acetaminophen or an antihistamine before, during or after treatment with the anti-CD52 antibody.
11. The method of claim 1, further comprising administering the anti-CD52 antibody at 1-12 mg/day for 1-5 days in one or more subsequent treatment cycles after the second treatment cycle, if the patient has renewed MS activity after the second treatment cycle.
12. The method of claim 1 or 2, wherein the anti-CD52 antibody is alemtuzumab.
13. The method of claim 1, wherein the patient has previously been treated with an MS drug that is not an anti-CD52 antibody.
14. The method of claim 13, wherein the patient has failed to respond to the previous MS treatment.
15. The method of claim 1, wherein the patient has a relapsing form of MS.
16. The method of claim 15, wherein the patient has relapsing-remitting MS.
17. The method of claim 15, wherein the patient has active relapsing MS.
18. The method of claim 1, wherein the patient is treated with a steroid before or during treatment with the anti-CD52 antibody.
19. The method of claim 1, wherein the period of time between the initial treatment cycle and the second treatment cycle is at least 6 months.
20. The method of claim 1, wherein the period of time between the initial treatment cycle and the second treatment cycle is at least 18 months.
21. The method of claim 1, wherein the period of time between the initial treatment cycle and the second treatment cycle is at least 24 months.
22. A method of treating multiple sclerosis (MS) in a patient with a single MS immunotherapeutic consisting of alemtuzumab, the method comprising:
    administering alemtuzumab to the patient at 12 mg/day for five consecutive days in an initial treatment cycle, and
    12 months after the initial treatment cycle, administering alemtuzumab to the patient at 12 mg/day for three consecutive days in a second treatment cycle.
23. The method of claim 22, wherein the 12 mg of alemtuzumab for each treatment day is administered to the patient via intravenous infusion.
24. The method of claim 22, wherein the patient is pre-medicated with a steroid immediately prior to alemtuzumab administration for the first three days of each treatment cycle.

25. The method of claim 22, wherein the patient has a relapsing form of MS.

26. A method of reducing the risk of relapse, or the risk of progression of clinically significant disability, in a multiple sclerosis (MS) patient with a single MS immunotherapeutic consisting of an anti-CD52 antibody, the method comprising:
administering the anti-CD52 antibody to the patient at 1-12 mg/day for 1-5 days in an initial treatment cycle, and
at least 3 months after the initial treatment cycle, administering the anti-CD52 antibody to the patient at 1-12 mg/day for 1-5 days in a second treatment cycle.

27. The method of claim 26, wherein the anti-CD52 antibody is alemtuzumab.

28. The method of claim 26, wherein the patient has a relapsing form of MS.

29. A method of treating multiple sclerosis (MS) in a patient with a single MS immunotherapeutic consisting of an anti-CD52 antibody, wherein the method comprises:
administering a total dose of 10-60 mg of the anti-CD52 antibody to the patient over 1-5 days in an initial treatment cycle, and
at least 3 months after the initial treatment cycle, administering a total dose of 10-60 mg of the anti-CD52 antibody to the patient over 1-5 days in a second treatment cycle.

30. The method of claim 29, wherein the anti-CD52 antibody is alemtuzumab.

31. The method of claim 29, wherein the patient has a relapsing form of MS.

32. The method of claim 22, 26, or 29, wherein the patient has previously been treated with an MS drug that is not an anti-CD52 antibody.

33. The method of claim 32, wherein the patient has failed to respond to the previous MS treatment.

34. The method of claim 22, 26, or 29, wherein the patient has not received prior MS therapy.

35. The method of claim 26 or 29, wherein the second treatment cycle is administered at least 12 months after the first treatment cycle.

36. The method of claim 22, 26, or 29, wherein the patient is treated with a steroid to manage infusion-related side effects.

37. The method of claim 1, 22, 26, or 29, wherein the two treatment cycles stabilize or decrease progression of neurological disability.

38. The method of claim 1, 22, 26, or 29, wherein the two treatment cycles stabilize or reduce central nervous system lesions as detected by imaging.

39. The method of claim 22, 26, or 29, further comprising administering the anti-CD52 antibody at 1-12 mg/day for 1-5 days in a further treatment cycle in response to renewed MS activity.

40. The method of claim 1, 22, 26, or 29, wherein the anti-CD52 antibody is administered to the patient in only the initial and second treatment cycles.

41. A method of treating a relapsing form of multiple sclerosis (MS) in a patient, the method comprising:
administering alemtuzumab to the patient at 12 mg/day for five consecutive days in an initial treatment cycle, and
12 months after the initial treatment cycle, administering alemtuzumab to the patient at 12 mg/day for three consecutive days in a second treatment cycle,
wherein the 12 mg of alemtuzumab for each treatment day is administered to the patient via intravenous infusion over a period of 4 hours, and
wherein the patient is pre-medicated with a steroid immediately prior to alemtuzumab administration for the first three days of each treatment cycle.

42. The method of claim 41, wherein the method produces a therapeutic effect within the treated patient that is sustained for at least 12 months after the second treatment cycle and the therapeutic effect is a reduction in the risk of relapse.

43. The method of claim 41, wherein the method produces a therapeutic effect within the treated patient that is sustained for at least 12 months after the second treatment cycle and the therapeutic effect is a reduction in the risk for progression of clinically significant disability.

44. The method of claim 41, wherein the steroid is methylprednisolone and is administered to the patient at 1 g/day intravenously.

45. The method of claim 41, wherein the patient is treated with acetaminophen or an antihistamine before, during or after treatment with alemtuzumab.

* * * * *